US00PP33866P2

(12) United States Plant Patent
Winner

(10) Patent No.: US PP33,866 P2
(45) Date of Patent: Jan. 11, 2022

(54) ***COREOPSIS* PLANT NAMED 'BALUPTRED'**

(50) Latin Name: ***Coreopsis* hybrid**
Varietal Denomination: Baluptred

(71) Applicant: Ball Horticultural Company, West Chicago, IL (US)

(72) Inventor: Blair Winner, Ventura, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/394,533

(22) Filed: Aug. 5, 2021

(51) Int. Cl.
*A01H 5/02* (2018.01)
*A01H 6/14* (2018.01)

(52) U.S. Cl.
USPC ..... Plt./417

(58) Field of Classification Search
USPC ..... Plt./417
See application file for complete search history.

*Primary Examiner* — Susan McCormick Ewoldt
(74) *Attorney, Agent, or Firm* — Audrey Charles

(57) ABSTRACT

A new and distinct cultivar of *Coreopsis* plant named 'Baluptred', characterized by its single-type, dark red colored inflorescences with yellow-orange colored tips, medium green colored foliage, and moderately vigorous, mounded growth habit, is disclosed.

1 Drawing Sheet

Latin name of genus and species of plant claimed: *Coreopsis* hybrid.

Variety denomination: 'Baluptred'.

BACKGROUND OF THE INVENTION

The present invention relates to a new and distinct cultivar of *Coreopsis* plant botanically known as *Coreopsis* hybrid and hereinafter referred to by the cultivar name 'Baluptred'.

The new cultivar originated in a controlled breeding program in Santa Paula, Calif. during June 2014. The objective of the breeding program was the development of *Coreopsis* cultivars having large inflorescences, substantially continuous blooming throughout the summer, and moderately vigorous, mounded growth habits.

The new *Coreopsis* cultivar is the result of self-pollination of the proprietary *Coreopsis* hybrid breeding selection coded 64839-1, not patented, characterized by its single-type, dark red colored inflorescences with yellow-orange colored tips, medium green colored foliage, and moderately vigorous, mounded growth habit. The new cultivar was selected as a single flowering plant within the progeny of the above stated self-pollination during October 2017 in a controlled environment in Santa Paula, Calif.

Asexual reproduction of the new cultivar by terminal stem cuttings since October 2017 in Santa Paula, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Baluptred' as a new and distinct cultivar of *Coreopsis* plant:

1. Single-type, dark red colored inflorescences with yellow-orange colored tips;
2. Medium green colored foliage; and
3. Moderately vigorous, mounded growth habit.

Plants of the new cultivar differ from plants of the parent primarily in having a larger dark red area on the ray florets and shorter peduncles.

Of the many commercially available *Coreopsis* cultivars, the most similar in comparison to the new cultivar is the *Coreopsis* cultivar UpTick Yellow & Red 'Baluptowed', U.S. Plant Pat. No. 28,865. However, in comparison, plants of the new cultivar differ from plants of 'Baluptowed' in at least the following characteristics:

1. Plants of the new cultivar have fewer ray florets than plants of 'Baluptowed';
2. Plants of the new cultivar have ray florets with darker yellow-orange color and a greater area of dark red color than plants of 'Baluptowed'; and
3. Plants of the new cultivar have smaller diameter inflorescences than plants of 'Baluptowed'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baluptred'. The plants were approximately 13-weeks old. The plants were grown for approximately 6 weeks in three-quart containers in an outdoor nursery in West Chicago, Ill. Plants were given two pinches prior to transplant and one pinch one week after transplant.

DETAILED BOTANICAL DESCRIPTION

Figure 1:
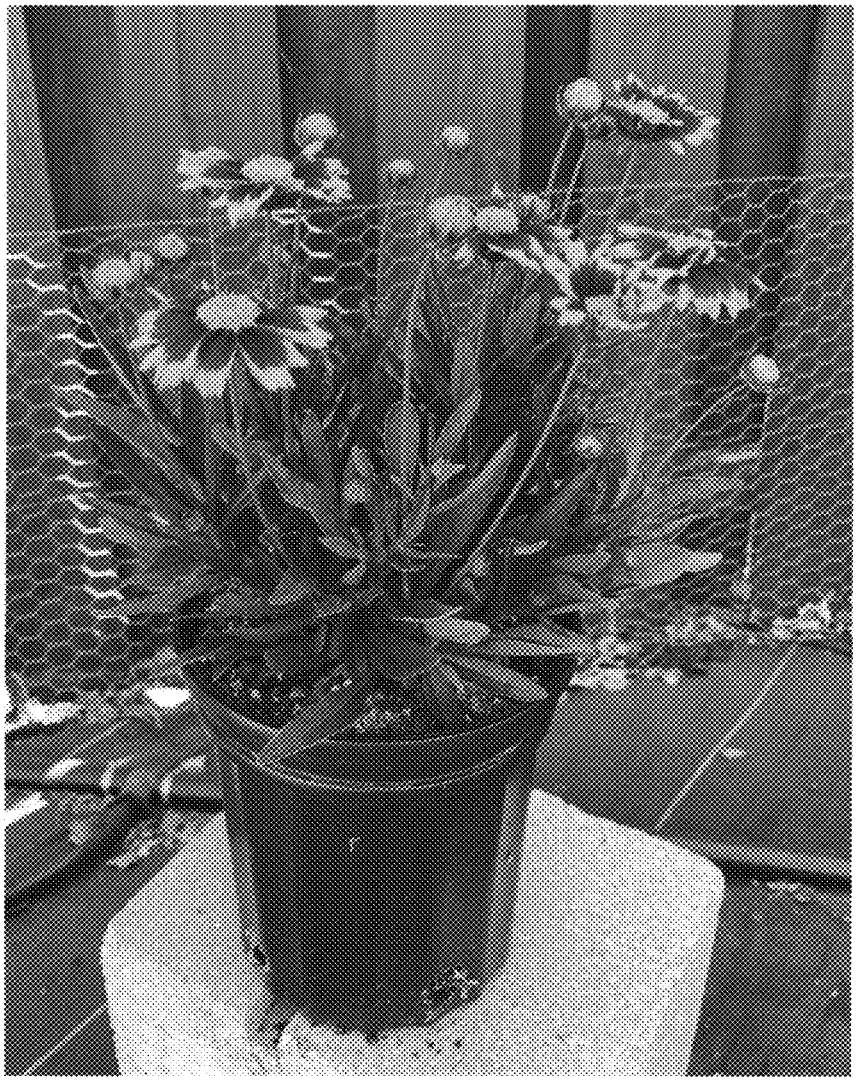
FIG. 1 illustrates a side view of the overall growth and flowering habit of 'Baluptred'.
Figure 2:
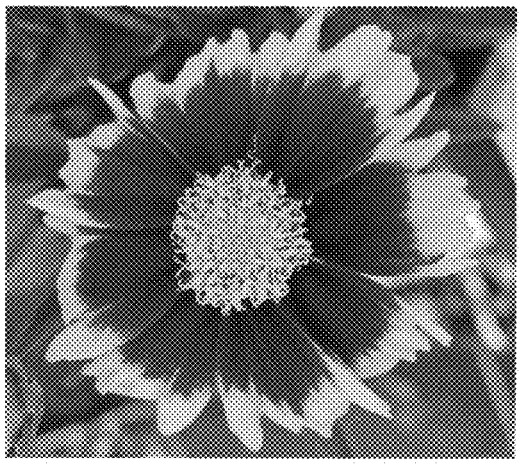
FIG. 2 illustrates a close-up view of an inflorescence of 'Baluptred'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2021 under natural light conditions in Naperville, Ill.

The following descriptions and measurements describe approximately 13 weeks old plants produced from cuttings from stock plants and grown under conditions comparable to those used in commercial practice. The plants were grown in three-quart containers for approximately 6 weeks in an outdoor nursery in West Chicago, Ill. Plants were given two pinches prior to transplant and one pinch one week after transplant. Prior to transplant plants were grown in liners in a poly-covered greenhouse in West Chicago, Ill. Greenhouse temperatures ranged from an average high of 79.5° F. (26.4° C.) to an average low of 68.5° F. (20.3° C.), and supplemental lighting was provided daily for five hours during short days. Measurements and numerical values represent averages of typical plants.

Botanical classification: *Coreopsis* hybrid 'Baluptred'.

Parentage:

*Female and male parent.*—Proprietary *Coreopsis* hybrid breeding selection coded 64839-1, not patented.

Propagation:

*Type cutting.*—Terminal stem.

*Time to initiate roots.*—Approximately 10 to 12 days at 70° F. (21° C.).

*Time to produce a rooted cutting.*—Approximately 5 to 6 weeks at 70° F. (21° C.).

*Root description.*—Fibrous, thin, white in color.

*Rooting habit.*—Freely branching, dense.

Plant description:

*Commercial crop time.*—Approximately 10 to 12 weeks from a rooted cutting to finish in a one-gallon container.

*Growth habit and general appearance.*—Herbaceous perennial, moderately vigorous, mounded growth habit.

*Hardiness.*—USDA Zone 5a (−20° F. to −15° F./−28.9° C. to −26° C.).

*Size.*—Height from soil level to top of plant plane: Approximately 22.0 cm. Width: Approximately 25.0 cm.

*Branching habit.*—Freely branching, pinching improves basal branching. Quantity of lateral branches per plant: 6 main branches each having approximately 4 lateral branches.

*Main branches.*—Strength: Moderately strong. Length to base of peduncle: Approximately 12.0 cm. Diameter: Approximately 3.0 mm. Length of central internode: Approximately 1.2 cm. Texture: Slightly glossy, glabrous. Color of young and mature stems: 146B.

Foliage description:

*General description.*—Quantity of leaves per main branch: Approximately 6. Type: Simple and trifoliate. Fragrance: None. Arrangement: Opposite. Aspect: Petiole is acute angle to stem; blade is at an acute angle to somewhat perpendicular to stem. Shape of leaf and leaflet: Elliptic. Margin of leaf and leaflet: Entire, ciliate. Apex of leaf and leaflet: Acute. Base of leaf and leaflet: Attenuate, simple leaf sessile. Venation pattern: Pinnate. Texture of upper and lower surfaces: Glabrous. Color of upper surface of young and mature foliage: NN137B with indistinguishable venation except for midvein of 146B. Color of lower surface of young and mature foliage: Closest to 137B with indistinguishable venation except for midvein of 146B.

*Simple leaf.*—Length: Approximately 9.0 cm. Width: Approximately 1.6 cm.

*Mature trifoliate leaf.*—Length of mature trifoliate leaf: Approximately 7.0 cm. Width of mature trifoliate leaf: Approximately 3.3 cm. Length of terminal leaflet: Approximately 4.7 cm. Width of terminal leaflet: Approximately 1.3 cm. Length of lateral leaflet: Approximately 1.6 cm. Width of lateral leaflet: Approximately 5.0 mm.

*Petiole of mature trifoliate leaf.*—Length: Approximately 2.2 cm. Diameter: Approximately 2.0 mm. Texture: Sparsely pubescent. Color of upper and lower surfaces: 146B.

Flowering description:

*Flowering habit.*—'Baluptred' is freely flowering under outdoor growing conditions with substantially continuous blooming from spring through autumn.

*Lastingness of individual inflorescence on the plant.*—Approximately 7 to 10 days.

Inflorescence description:

*General description.*—Type: Daisy-type composite, actinomorphic. Persistent. Shape: Round. Aspect: Erect. Arrangement: Terminal capitulum, positioned above the foliage. Quantity per plant: Approximately 7. Diameter: Approximately 5.0 cm. Depth: Approximately 1.5 cm. Fragrance: Slightly acrid.

*Peduncle.*—Strength: Strong, flexible. Aspect: Erect. Length: Approximately 9.5 cm. Diameter: Approximately 2.0 mm. Texture: Glabrous, slightly glossy. Color: 146B.

*Bud.*—Rate of opening: Generally takes 4 to 5 days for bud to progress from first color to fully open inflorescence. Quantity per plant: Approximately 13.

*Bud just before opening.*—Shape: Oblate. Width: Approximately 1.2 cm. Depth: Approximately 1.0 cm. Color: 152B to 152C.

*Ray florets.*—Quantity per inflorescence: Approximately 8. Arrangement: In a single whorl, imbricate. Aspect: Flattened to slightly twisted. Shape: Obovate. Margin: Entire. Apex: Incised. Base: Rounded. Length: Approximately 2.3 cm. Width: Approximately 1.7 cm. Texture of upper and lower surfaces: Glabrous, abaxially ribbed. Color of upper surface when first open: 187A with tips of 17A. Color of lower surface when first and fully open: 17B with an underlay of 187B, tips of 17B. Color of upper surface when fully open: 187A to 187B with tips of 17A.

*Disc florets.*—Quantity per inflorescence: Approximately 160. Arrangement: Massed in center of inflorescence. Shape: Tubular, approximately lower 90% fused. Margin: Entire. Apex: Five acute tips. Base: Fused. Length: Approximately 9.0 mm. Diameter at tube opening: Approximately 2.0 mm. Diameter at base: Approximately 1.0 mm. Texture of outer surface: Glabrous. Texture of inner surface: Glabrous with glandular pubescence on tips. Color of upper or inner surface when first and fully open: Closest to 154D, translucent with tips of 17A. Color of lower or outer surface when fully open: Closest to 154D, translucent with tips of 17B and base of 145C.

*Disc.*—Diameter: Approximately 1.5 cm. Depth: Approximately 7.0 mm.

*Receptacle.*—Shape: Dome. Height: Approximately 2.0 mm. Diameter at base: Approximately 5.0 mm. Color: 145D.

*Phyllaries.*—Quantity per inflorescence Approximately 16. Arrangement: In two equally divided whorls. Base of inner whorl fused into cup-shaped base surrounding receptacle, non-imbricate, held close to ray florets.

*Outer phyllaries.*—Shape: Lanceolate. Margin: Entire, ciliate. Apex: Acute. Base: Truncate. Length: Approximately 1.1 cm. Width: Approximately 3.0 mm. Texture of upper and lower surfaces: Glabrous, glossy. Color of upper and lower surfaces: 137A.

*Inner phyllaries.*—Shape of free portion: Ovate. Margin: Entire. Apex: Acute. Base: Fused. Length: Approximately 1.5 cm. Width: Approximately 6.0 mm. Texture of upper and lower surfaces: Glabrous. Color of upper and lower surfaces: 152D with cup-shaped portion of closest to 144A.

*Reproductive organs.*—Androecium: Present on disc florets only. Stamen quantity: 5. Stamen length: Approximately 6.0 mm. Filament length: Approximately 3.0 mm. Filament color: 154D. Anther shape: Oblong, basifixed. Anther length: Approximately 3.0 mm. Anther color: 154D, translucent, tinted with 187B. Pollen amount: Abundant. Pollen color: 17A. Gynoecium: Present on disc florets only. Pistil quantity: 1 per floret. Pistil length: Approximately 9.0 mm. Stigma shape: 2-branched. Stigma length: Each branch approximately 2.0 mm. Stigma color: 17B. Style length: Approximately 7.0 mm. Style color: 17C. Ovary length: Approximately 1.0 mm. Ovary color: 145C.

Seed and fruit production: Neither seed nor fruit production has been observed.

Disease and pest resistance: Resistance to pathogens and pests common to *Coreopsis* has not been observed.

What is claimed is:

1. A new and distinct cultivar of *Coreopsis* plant named 'Baluptred', substantially as herein illustrated and described.

* * * * *